United States Patent [19]

Hänel et al.

[11] Patent Number: 5,494,658
[45] Date of Patent: Feb. 27, 1996

[54] ANTIDANDRUFF AGENTS AND COSMETIC PREPARATIONS

[75] Inventors: Heinz Hänel, Oberursel-Stierstadt; Waltraud Simsch; Alwin K. Reng, both of Kelkheim, all of Germany

[73] Assignee: Hoechst Aktiengesellschaft, Frankfurt am Main, Germany

[21] Appl. No.: 317,030

[22] Filed: Oct. 3, 1994

[30] Foreign Application Priority Data

Oct. 5, 1993 [DE] Germany .......................... 43 33 893.3

[51] Int. Cl.⁶ .............................. A61K 7/06; A61K 7/08; A61K 7/32
[52] U.S. Cl. .................. 424/70.1; 424/65; 424/401; 424/70.21; 424/70.22; 424/70.24; 424/70.31; 514/880; 514/881
[58] Field of Search .............. 424/401, 65, 70.1, 424/70.21, 70.24, 70.31, 70.22; 514/345, 880, 881

[56] References Cited

U.S. PATENT DOCUMENTS

| | | | |
|---|---|---|---|
| 4,185,106 | 1/1980 | Dittmar et al. | 424/263 |
| 4,797,409 | 1/1989 | Lohaus et al. | 514/345 |

FOREIGN PATENT DOCUMENTS

| | | |
|---|---|---|
| 1302415 | 6/1992 | Canada . |
| 0241918 | 10/1987 | European Pat. Off. . |
| 0386900 | 9/1990 | European Pat. Off. . |
| 2234009 | 1/1979 | Germany . |

OTHER PUBLICATIONS

EPO241918 (Oct. 21, 1987) Abstract.
DE 2,234,009 (Jan. 11, 1979) Abstract.
European Search Report, Dec. 28, 1994, No. 94115183.9.
Mycoses, Bd. 34, Nr. Supl, 1991.
Database WPI Derwent Publications Ltd., AN 84-033065 (JP 58,222 010) .

*Primary Examiner*—Jyothsna Venkat
*Attorney, Agent, or Firm*—Connolly & Hutz

[57] ABSTRACT

The invention relates to cosmetic preparations which have a content of compounds of the general formula I

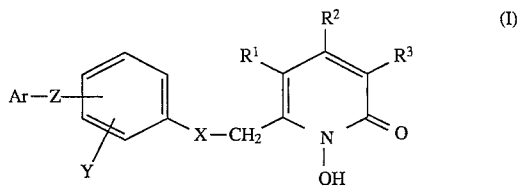

in which $R^1$, $R^2$ and $R^3$ are identical or different and are hydrogen or alkyl with 1 to 4 carbon atoms, where $R^1$ and $R^3$ are preferably hydrogen and $R^2$ is preferably methyl, X is S or O, Y is hydrogen or up to two halogen atoms, preferably chlorine and/or bromine, Z is a single bond or the divalent radicals O, S, —$CH_2$—, —$CH_2$—O—, —O—$CH_2$—, —$CH_2$—S—, —S—$CH_2$— or —CH=CH—$CH_2$—O—, Ar is an aromatic ring system which has up to two rings and which can be substituted by up to three radicals from the group comprising fluorine, chlorine, bromine, methoxy, $C_1$–$C_4$-alkyl, trifluoromethyl and trifluoromethoxy, and/or their salts.

The invention furthermore relates to the use of these cosmetic preparations as antidandruff composition and deodorant cosmetic composition.

7 Claims, No Drawings

ANTIDANDRUFF AGENTS AND COSMETIC PREPARATIONS

DE-C 22 34 009 discloses cosmetic preparations which are characterized by a content of compounds of the formula II

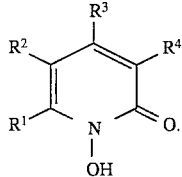

In the above formula II, $R^1$ is, inter alia, aryloxyalkyl with alkyl of 1 to 4 carbon atoms, $R^2$ is, inter alia, hydrogen, alkyl with 1 to 4 carbon atoms, $R^3$ is, inter alia, hydrogen, alkyl with 1 to 4 carbon atoms and $R^4$ is, inter alia, hydrogen, alkyl with 1 to 4 carbon atoms.

The radical $R^1$ is specifically stated to be only phenyloxymethyl.

EP-A 0 241 918 discloses compounds of the formula I

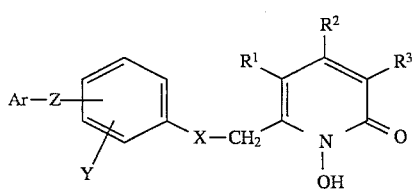

in which $R^1$, $R^2$ and $R^3$ are identical or different and are hydrogen or alkyl with 1 to 4 carbon atoms, where $R^1$ and $R^3$ are preferably hydrogen and $R^2$ is preferably methyl, is S or, preferably, O, Y is hydrogen or up to two halogen atoms, preferably chlorine and/or bromine, Z is a single bond or the divalent radicals O, S, —$CH_2$—, —$CH_2$—O—, —O—$CH_2$—, —$CH_2$—S—, —S—$CH_2$— or —CH=CH—$CH_2$—O—, Ar is an aromatic ring system which has up to two rings and which can be substituted by up to three radicals from the group comprising fluorine, chlorine, bromine, methoxy, $C_1$–$C_4$-alkyl, trifluoromethyl and trifluoromethoxy.

As important representatives of the class of compounds characterized by formula I, inter alia 6-[4-(4-chlorophenoxy)phenoxymethyl]-1-hydroxy-4-methyl-2-pyridone is mentioned. This compound is called rilopirox hereinafter for simplicity.

The compounds of the formula I have topical antimycotic properties with a broad spectrum of action against pathogenic fungi which affect both the skin and the mucosa, such as yeasts and molds. These compounds can therefore be used to control infections by these pathogens in human and veterinary medicine. The use can take place as free hydroxypyridones or in the form of their physiologically tolerated salts with inorganic or organic bases in the formulations customary for controlling fungi, such as solutions, suspensions, creams, ointments, powders or suppositories (pessaries).

EP-A 0 241 918 merely discloses the use of the compounds of the formula I as pharmaceuticals.

The object of the present invention now comprises making available cosmetic preparations, in particular antidandruff compositions and deodorant cosmetic compositions.

The present invention relates to cosmetic preparations which have a content of compounds of the formula I

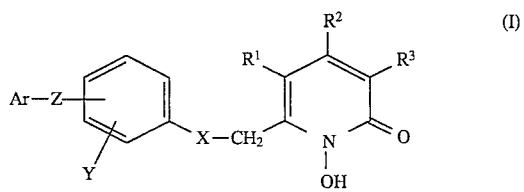

in which $R^1$, $R^2$ and $R^3$ are identical or different and are hydrogen or alkyl with 1 to 4 carbon atoms, where $R^1$ and $R^3$ are preferably hydrogen and $R^2$ is preferably methyl, X is S or, preferably, O, Y is hydrogen or up to two halogen atoms, preferably chlorine and/or bromine, Z is a single bond or the divalent radicals O, S, —$CH_2$—, —$CH_2$—O—, —O—$CH_2$—, —$CH_2$—S—, —S—$CH_2$— or —CH=CH—$CH_2$—O—, Ar is an aromatic ring system which has up to two rings and which can be substituted by up to three radicals from the group comprising fluorine, chlorine, bromine, methoxy, $C_1$–$C_4$-alkyl, trifluoromethyl and trifluoromethoxy, and/or their salts.

The term aromatic ring systems embraces phenyl and fused systems such as naphthyl, tetrahydronaphthyl and indenyl, as well as isolated systems derived from biphenyl, diphenylalkanes, diphenyl ethers and diphenyl thioethers.

These cosmetic preparations are preferably used as antidandruff composition or deodorant cosmetic composition.

The following compound may be mentioned as preferred example of a substance which can be used according to the invention as active substance in the cosmetic preparations:

6-[4-(4-chlorophenoxy)phenoxymethyl]-1-hydroxy-2-pyridone (called: rilopirox)

The abovementioned compounds can be used both in free form and as salts.

If organic bases are used, bases of low volatility are preferably used, such as, for example, low molecular weight alkanolamines such as, for example, ethanolamine, diethanolamine, N-ethylethanolamine, N-methyldiethanolamine, triethanolamine, diethylaminoethanol, 2-amino-2-methyl-n-propanol, dimethylaminopropanol, 2-amino-2-methylpropanediol and triisopropanolamine. Other bases of relatively low volatility which may be mentioned are, for example, ethylenediamine, hexamethylenediamine, morpholine, piperidine, piperazine, cyclohexylamine, tributylamine, dodecylamine, N,N-dimethyldodecylamine, stearylamine, oleylamine, benzylamine, dibenzylamine, N-ethylbenzylamine, dimethylstearylamine, N-methylmorpholine, N-methylpiperazine, 4-methylcyclohexylamine and N-hydroxyethylmorpholine. It is also possible to use the salts of quaternary ammonium hydroxides such as, for example, trimethylbenzylammoniumhydroxide, tetramethylammonium hydroxide or tetraethylammonium hydroxide, furthermore guanidine and its derivatives, in particular its alkylation products. However, it is also possible, for example, to use low molecular weight alkylamines such as, for example, methylamine, ethylamine or triethylamine as salt formers. Also suitable for the compounds to be used according to the invention are salts with inorganic cations such as, for example, alkali metal salts, in particular sodium, potassium or ammonium salts, alkaline earth metal salts such as, in particular, magnesium or calcium salt, and salts with cations with 2 to 4 charges, such as, for example, the zinc, aluminum or zirconium salt.

The active substances of the formula reproduced above which are to be used in the cosmetic preparations can be prepared, for example, by processes as described in US Pat. No. 4,797,409. The abovementioned salts are prepared in a known manner by mixing preferably equimolar amounts of the salt-forming components.

A wide variety of cosmetic preparations are suitable, in particular shampoos, for the use according to the invention of the said compounds. Examples of other preparations which are suitable according to the invention and which may be mentioned are the following hair care and hairdressing compositions: hair rinses, hair tonics, hair regenerating compositions, hair lotions, water wave lotions, hair sprays, hair creams, hair gels, hair oils, hair pomades or hair brilliantines. Accordingly, these are always preparations which are applied to the hair and the scalp for a shorter or longer time depending on the actual purpose for which they are used. Addition of the compounds according to the invention then effects simultaneous dandruff treatment. However, it is also possible to produce preparations which are used primarily or exclusively for the purpose of eliminating dandruff.

If the antidandruff preparations according to the invention are supplied as shampoos, these can be clear liquids, opaque liquids (with pearly luster effect), in cream form, gel-like or else in powder form or in tablet form, and as aerosols. The detergent raw materials on which these shampoos are based can be anionic, cationic, nonionic and amphoteric in nature and also be present in combinations of these substances.

Examples of anionic detergent substances of this type which may be mentioned are: $C_{10}$–$C_{20}$-alkyl- and alkylenecarboxylates, alkyl ether carboxylates, fatty alcohol sulfates, fatty alcohol ether sulfates, alkylolamide sulfates and sulfonates, fatty acid alkylolamide polyglycol ether sulfates, alkanesulfonates and hydroxyalkanesulfonates, olefinsulfonates, acyl esters of isethionates, α-sulfo fatty acid esters, alkylbenzenesulfonates, alkylphenol glycol ether sulfonates, sulfosuccinates, sulfosuccinic monoesters and diesters, fatty alcohol ether phosphates, protein-fatty acid condensation products, alkyl monoglyceride sulfates and sulfonates, alkyl glyceride ether sulfonates, fatty acid methyltaurides, fatty acid sarcosinates, and sulforicinoleates. These compounds and their mixtures are used in the form of their salts which are soluble in water or dispersible in water, for example the sodium, potassium, magnesium, ammonium, mono-, di- and triethanolammonium and analogous alkylanunonium salts.

Examples of suitable cationic surfactants are quaternary ammonium salts such as di($C_{10}$–$C_{24}$-alkyl)dimethylammonium chloride or bromide, preferably di ($C_{12}$–$C_{18}$-alkyl) -dimethylammonium chloride or bromide; $C_{10}$–$C_{24}$-alkyldimethylethylammonium chloride or bromide; $C_{10}$–$C_{24}$-alkyltrimethylammonium chloride or bromide, preferably cetyltrimethylammonium chloride or bromide and $C_{20}$–$C_{24}$-alkyltrimethylammonium chloride or bromide; $C_{10}$–$C_{24}$-alkyldimethylbenzylammonium chloride or bromide, preferably $C_{12}$–$C_{18}$-alkyldime methylbenzylammoniumchloride; N-($C_{10}$–$C_{18}$-alkyl)pyridinium chloride or bromide, preferably N- ($C_{12}$–$C_{16}$-alkyl)pyridinium chloride or bromide; N-($C_{10}$–$C_{18}$-alkyl)isoquinolinium chloride, bromide or monoalkyl sulfate; N-($C_{12}$–$C_{18}$-alkyloylcolaminoformylmethyl)pyridinium chloride; N_($C_{12}$–$C_{18}$-alkyl)-N-methylmorpholinium chloride, bromide or monoalkyl sulfate; N-($C_{12}$–$C_{18}$-alkyl)-N-ethylmorpholinium chloride, bromide or monoalkyl sulfate; $C_{16}$–$C_{18}$-alkylpentaoxethylammonium chloride; diisobutylphenoxyethoxyethyldimethylbenzylammonium chloride; salts of N,N-diethylaminoethylstearylamide and oleylamide with hydrochloric acid, acetic acid, lactic acid, citric acid, phosphoric acid; N-acylamidoethyl-N,N-diethyl-N-methylammonium chloride, bromide or monoalkylsulfate and N-acylaminoethyl-N,N-diethyl-N-benzylammonium chloride, bromide or monoalkyl sulfate, where acyl is preferably stearyl or oleyl.

Examples of suitable nonionic surfactants which can be used as detergent substances are: fatty alcohol ethoxylates (alkylpolyethylene glycols); alkylphenol polyethylene glycols; alkyl mercaptan polyethylene glycols; fattyamine ethoxylates (alkylaminopolyethylene glycols); fatty acid ethoxylates (acylpolyethylene glycols); polypropylene glycol ethoxylates (Pluronic); fatty acid alkylolamides (fatty acid amide polyethylene glycols); sucrose esters; sorbitol esters and polyglycol ether.

Examples of amphoteric surfactants which can be added to the shampoos are: N-($C_{12}$–$C_{18}$-alkyl)-β-aminopropionates and N-($C_{12}$–$C_{18}$-alkyl)-β-iminodipropionates as alkali metal and mono-, di- and trialkylammonium salts; N-acylamidoalkyl- N,N-dimethylacetobetaine, preferably N-($C_8$–$C_{18}$-acyl)amidopropyl-N, N-dimethylacetobetaine; $C_{12}$–$C_{18}$-alkyldimethylsulfopropylbetaine; amphoteric surfactants based on imidazoline (commercial name: Miranol®, Steinapon®), preferably the sodium salt of 1-(β-carboxymethyloxyethyl)-1-(carboxymethyl)-2-1laurylimidazolinium;
amine oxide, for example $C_{12}$–$C_{18}$-alkyldimethylamine oxide, fatty acid amidoalkyldimethylamine oxide.

The preparations according to the invention can additionally contain further additives customary in cosmetics, for example perfumes, colorants, also those which simultaneously dye or tint the hair, solvents, opacifying agents and pearly luster agents, for example esters of fatty acids with polyols, magnesium and zinc salts of fatty acids, dispersions based on copolymers, thickening agents such as sodium, potassium and ammonium chloride, sodium sulfate, fatty acid alkylolamides, cellulose derivatives, natural rubbers, also plant extracts, protein derivatives such as gelatin, collagen hydrolysates, polypeptides with a natural or synthetic basis, egg yolk, lecithin, lanolin and lanolin derivatives, fats, oils, fatty alcohols, silicones, deodorizing agents, substances with antimicrobial activity, substances with antiseborrhoeic activity, substances with keratolytic and keratoplastic effect, such as, for example, sulfur, salicylic acid and enzymes.

For the preparation of the cosmetic preparations the active substance is dissolved under stirring at a temperature in the range between 20 and 60° C., preferably at room temperature, in the detergent substance used. Subsequently, the further additives are added.

In the event of alcohol containing cosmetic preparations the active substance is dissolved in the alcohol at a temperature in the range between 20 and 40° C., preferably at room temperature. Subsequently, the further additives are added. In the event of hair rinses and oil-in-water emulsions the active substance is dissolved in the fatty phase, which means together with the oil and the emulgator, at a temperature in the range between 70 and 90° C., preferably at 75° C. Subsequently, hot water is added and the emulsion is stirred and cooled.

The shampoos are produced in a manner known per se by mixing the individual components and—where necessary further—processing appropriate for the particular type of preparation. Some of this wide variety of possible formulations are described by way of example in the exemplary embodiments.

Examples of other hair cosmetic preparations in which the 1-hydroxy-2-pyridones can be used according to the invention and which may be mentioned are: hair rinses, hair lotions and hair regenerating compositions, which are rinsed off from the hair after a certain time or, depending on the formulation, can also remain on the hair. These products contain, inter alia, substances from the group of the abovementioned cationic surfactants which display a reviving and antistatic property on the hair.

The antidandruff preparations according to the invention can also be supplied in the form of aqueous and aqueous alcoholic hair lotions, water wave lotions (hair setting compositions), also those in gel form, and in aerosol form as hair spray, as well as in the form of hair care and hairdressing creams and gels. Ethanol and isopropanol are preferably used as alcohols.

Examples of resins with hair-setting and hair style setting action, which can be present in a concentration of 0.5 to 6% by weight, preferably 1 to 3% by weight, in the appropriate preparations (hair setting compositions, hair spray) are: shellac and derivatives thereof, reaction products of rosin with acrylic acid, poly-N-vinylpyrrolidone and alkyl-substituted poly-N-vinylpyrrolidone, poly-N-vinyl-N-alkylacetamide, polyvinyl acetate and partially hydrolyzed polyvinyl acetate, polyvinyl alcohol, alkyl esters of acrylic acid, copolymers of vinyl acetate and N-vinyl-N-alkylacetamide, copolymers of vinyl acetate and N-vinylpyrrolidone, reaction products of copolymers of vinyl acetate and acrylic acid or crotonic acid with organic bases, copolymers of vinyl acetate and maleic monoester, copolymers of vinyl acetate, vinyl pivalate and crotonic acid, copolymers of fatty acid vinyl esters and (meth)acrylic acid, copolymers of (meth) acrylic esters and N-vinylpyrrolidone, copolymers of acrylic esters and (meth)acrylic acid, alkyl esters of copolymers of methyl vinyl ether and maleic anhydride, alkyl esters of copolymers of olefins and maleic anhydride, polyvinylacetals and polyvinylbutyrals, dimethylhydantoin-formaldehyde condensates, cyclohexanone-formaldehyde resins, phthalate resins, protein hydrolysates and protein derivatives, starch and cellulose derivatives, which may also contain cationic groups, and other film-formers with quaternary groups such as reaction products of copolymers of alkyl(meth)acrylates and dimethylaminoethyl(meth) acrylate with alkylating agents, furthermore quaternary copolymers of N-vinylpyrrolidone and dialkylaminoalkyl-(meth)acrylates.

It is furthermore possible to incorporate the compounds which can be used according to the invention in anhydrous oily preparations such as hair oil, hair pomade and hair brilliantine.

All these preparations are also produced—as already mentioned for the shampoo—in a manner known per se with the addition of the active substance used according to the invention. The antidandruff preparations according to the invention can contain of the abovementioned 1-hydroxy-2-pyridones one compound or else several in combination.

The antidandruff active substance is incorporated in the preparations according to the invention in amounts which are normally between about 0.05 and about 10%. Within this range, the concentrations of the specific preparations depend on the purpose for which they are used. Certain formulations such as, for example, concentrates which must be diluted before they are used may also have considerably higher concentrations.

If the preparations remain on the hair, such as, for example, hair lotions, hair setting compositions, creams, etc., lower concentrations will be used, for example of about 0.01 to about 1%, preferably 0.1 to 0.5%. They are expediently used in higher concentrations if the cosmetic preparations act, where appropriate after dilution, for only a short time on the hair and scalp, such as, for example, shampoos or hair rinses. In these cases, for example, concentrations of about 0.2 to about 10%, preferably about 0.5 to about 2%, may be expedient.

It is known that 1-hydroxy-2-pyridinethiones and their salts, in particular the zinc salt, are active against dandruff. It was not to be expected that the sulfur-free compounds also show according to the invention an excellent antidandruff action.

The use according to the invention of the said 1-hydroxy-2-pyridones has numerous advantages in particular by comparison with the prior art mentioned.

The following may be picked out:

low use concentrations broad spectrum of antimicrobial action low toxicity.

The following examples illustrate the present invention. The stated amounts are based on weight.

EXAMPLE 1

Cream shampoo

| | |
|---|---|
| Rilopirox | 0.2% |
| Fatty acid methyltauride sodium salt | 70% |
| (® Hostapon CT paste, Hoechst AG) | |
| Fatty acid methylisethionate sodium salt | 5% |
| (® Hostapon SCID, Hoechst AG) | |
| Palm kernel fatty acid sarcoside | 5% |
| (® Medialan LD) | |
| Water | ad 100% |

EXAMPLE 2

Antidandruff shampoo

| | |
|---|---|
| Rilopirox | 0.3% |
| Fatty acid monoethanolamide polyglycol ether | 5% |
| (® Genagen CA-050, Hoechst AG) | |
| Alkyl ether sulfate sodium salt | 35.0% |
| (® Genapol LRO liquid, Hoechst AG) | |
| Acylaminopolyglycol ether sulfate | |
| magnesium salt | 10.0% |
| (® Genapol AMG, Hoechst AG) | |
| Alkylamidopropyl betaine | 8.0% |
| (® Genagen CAB, Hoechst AG) | |
| Bodying agent | 2.0% |
| (® Genapol L-3, Hoechst AG) | |
| Sodium chloride | 0.7% |
| Water | ad 100% |

EXAMPLE 3

"3 in 1 shampoo"

| | |
|---|---|
| Rilopirox | 0.2% |
| Alkyl ether sulfate sodium salt | 35.0% |
| (® Genapol LRO liquid, Hoechst AG) | |
| Acylaminopolyglycol ether sulfate | 5.0% |
| magnesium salt | |
| (® Genapol AMG, Hoechst AG) | |
| Fatty acid glutamate sodium salt | 5.0% |
| (® Hostapon KCG, Hoechst AG) | |
| Fatty acid-protein condensate | 5.0% |
| (® Hostapon SCHC, Hoechst AG) | |
| Silicone oil | 2.0% |
| (® Belsil DNC 6032, Wacker Chemie) | |
| D-Panthenol | 1.0% |
| Bodying agent | 2.5% |
| (® Genapol L-3, Hoechst AG) | |
| Alkylamidopropyl betaine | 8.0% |

| | |
|---|---|
| (® Genagen CAB, Hoechst AG) | |
| Sodium chloride | 2.0% |
| Water | ad 100% |

EXAMPLE 4

Shampoo concentrate

| | |
|---|---|
| Rilopirox | 0.2% |
| Alkyl ether sulfate sodium salt | 20.0% |
| (® Genapol LRO paste, Hoechst AG) | |
| Alkylamidopropyl betaine | 33.0% |
| (® Genapol CAB, Hoechst AG) | |
| Fatty acid monoethanolamide polyglycol ether | 5.0% |
| (® Genagen CA-050, Hoechst AG) | |
| Fatty acid-protein condensate | 5.5% |
| (® Hostapon SCHCP, Hoechst AG) | |
| Bodying agent | 3.0% |
| (® Genapol L-3, Hoechst AG) | |
| Water | ad 100% |

EXAMPLE 5 liquid soap

| | |
|---|---|
| Rilopirox | 0.1% |
| Alkyl ether sulfate sodium salt | 40.0% |
| (® Genapol LRO, Hoechst AG) | |
| sec. n-Alkylsulfonate sodium salt | 8.0% |
| (® Hostapur SAS, Hoechst AG) | |
| Bodying agent | 3.0% |
| (® Genapol L-3, Hoechst AG) | |
| Sodium chloride | 1.5% |
| Water | ad 100% |

EXAMPLE 6 deodorant soap

| | |
|---|---|
| Rilopirox | 0.2% |
| Basic soap | 99.8% |

EXAMPLE 7 roll-on deodorant

| | |
|---|---|
| Rilopirox | 0.1% |
| Hydroxyethyl cellulose ether | 0.7% |
| (® Tylose H 10000, Hoechst AG) | |
| Ethanol | 40.0% |
| 1,2-Propylene glycol | 5.0% |
| Solubilizer | 0.5% |
| (® Cremophor RH 455, BASF AG) | |
| Water | 53.0% |

EXAMPLE 8 deodorant

| | |
|---|---|
| Rilopirox | 0.15% |
| Ethanol | 70.0% |
| Superfatting agent | 0.5% |
| (® Softigen 767, Chem. Werke Hüls) | |
| Perfume oil | 0.5% |
| Allantoin | 0.1% |
| Water | ad 100% |

EXAMPLE 9 intimate cleanser

| | |
|---|---|
| Rilopirox | 0.1% |
| Acylaminopolyglycol ether sulfate magnesium salt | 40.0% |
| (® Genapol AMG, Hoechst AG) | |
| Bodying agent | 3.0% |
| (Glucamate DOE 120, Amercol) | |
| Water | ad 100% |

EXAMPLE 10 hair after-rinse

| | |
|---|---|
| Rilopirox | 0.2% |
| Cetyl alcohol | 2.5% |
| Liquid paraffin | 1.5% |
| Phosphoric ester compound | 1.5% |
| (® Hostaphat KL340N, Hoechst AG) | |
| Alkylpolyethoxyammonium lactate | 7.0% |
| (® Genamin KSL, Hoechst AG) | |
| Hydroxyethyl cellulose ether | 0.6% |
| (® Tylose, Hoechst AG) | |
| Water | ad 100% |

EXAMPLE 11 hair lotion

| | |
|---|---|
| Rilopirox | 0.05% |
| Fatty acid polyglycol ether | 0.6% |
| (® Emulsogen EL, Hoechst AG) | |
| Ethanol | 40.0% |
| Alkylpolyethoxyammonium lactate | 0.3% |
| (® Genamin KSL, Hoechst AG) | |
| D-Panthenol | 0.5% |
| Water | ad 100% |

EXAMPLE 12 hair setting composition

| | |
|---|---|
| Rilopirox | 0.05% |
| Isopropanol | 40.0% |
| Polyethylene glycol ($\bar{M}_w$ = 400) | 0.5% |
| Alkylpolyethoxyammonium lactate | 0.7% |
| (® Genamin KSL, Hoechst AG) | |
| Superfatting agent | 0.6% |
| Polyvinylpyrrolidone | 5.5% |
| (® Luviskol, BASF AG) | |
| Water | ad 100% |

EXAMPLE 13 face lotion

| | |
|---|---|
| Rilopirox | 0.05% |
| Ethanol | 30.0% |
| Superfatting agent | 0.2% |
| D-Panthenol | 0.5% |
| 1,2-Propylene glycol | 5.0% |

-continued

| Allantoin | 0.1% |
| Extrapon Hamamelis | 5.0% |
| Water | ad 100% |

EXAMPLE 14 oil-in-water cream

| Rilopirox | 0.1% |
| 1,2-Propylene glycol | 10.0% |
| Oil-in-water emulsifier | 12.0% |
| (® Hostacerin CG, Hoechst AG) | |
| Oil component | 8.0% |
| (® Entanol G, Henkel KG & A) | |
| Liquid paraffin | 5.0% |
| Isopropyl isostearate | 5.0% |
| Bodying agent | 0.3% |
| (® Carbopol 940, Goodrich) | |
| Sodium hydroxide solution (10% strength) | 0.4% |
| Water | ad 100% |

We claim:

1. A cosmetic preparation comprising, a compound present in an amount of from 0.05 to 10% of the formula I

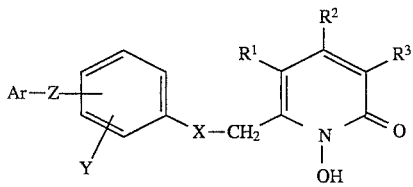

in which $R^1$, $R^2$, and $R^3$ are identical or different and are hydrogen or alkyl with 1 to 4 carbon atoms, X is S or O, Y is hydrogen or up to two halogen atoms, Z is a single bond or the divalent radicals O, S, —$CH_2$—, —$CH_2$—O—, —O—$CH_2$—, —$CH_2$—S—, —S—$CH_2$— or —CH=CH—$CH_2$—O—, Ar is an aromatic ring system which is phenyl, naphthyl, tetrahydronaphthyl, indenyl, biphenyl, diphenylether, or diphenylthioether and which can be substituted by up to three radicals selected from the group consisting of fluorine, chlorine, bromine, methoxy, $C_1$–$C_4$-alkyl, trifluoromethyl, and trifluoromethoxy, and their salts, or compounds of formula I or their salts, said compound of the formula I being present in sufficient quantity to have an antidandruff effect, and a detergent raw material selected from the group consisting of anionic, cationic, nonionic and amphoteric detergent substances for application to the hair and scalp.

2. A cosmetic preparation as claimed in claim 1, wherein $R^1$ and $R^3$ are hydrogen and $R^2$ is methyl.

3. A cosmetic preparation as claimed in claim 1, wherein Y is chlorine or bromine, Y is chlorine and bromine.

4. A cosmetic preparation as claimed in claim 1, wherein the compound is present in an amount of from 0.01 to 1%.

5. A cosmetic preparation as claimed in claim 1, wherein the compound of the formula I is 6-[4-(4-chlorophenoxy)phenoxymethyl]-1-hydroxy-4-methyl-2-pyridone.

6. A cosmetic preparation as claimed in claim 1, wherein the compounds of the formula I are present as their salts.

7. A cosmetic preparation as claimed in claim 1, wherein the compounds of the formula I are present as a mixture of compounds of the formula I and their salts.

* * * * *